United States Patent
Hauer et al.

(10) Patent No.: US 9,095,703 B2
(45) Date of Patent: Aug. 4, 2015

(54) SELF-DISSOLVING ELECTRODE OR PROBE IMPLANT

(75) Inventors: Marc Hauer, Zurich (CH); Thomas Doerr, Berlin (DE)

(73) Assignee: BIOTRONIK SE & Co. KG, Berlin (DE)

(*) Notice: Subject to any disclaimer, the term of this patent is extended or adjusted under 35 U.S.C. 154(b) by 97 days.

(21) Appl. No.: 13/338,404

(22) Filed: Dec. 28, 2011

(65) Prior Publication Data

US 2012/0185024 A1 Jul. 19, 2012

Related U.S. Application Data

(60) Provisional application No. 61/432,213, filed on Jan. 13, 2011.

(51) Int. Cl.
*A61N 1/00* (2006.01)
*A61N 1/05* (2006.01)

(52) U.S. Cl.
CPC .......... *A61N 1/057* (2013.01); *A61N 2001/0578* (2013.01)

(58) Field of Classification Search
CPC ... A61N 1/057; A61N 1/0575; A61N 1/0539; A61N 1/0536; A61N 2001/0578; A61N 1/0558; A61N 1/059
USPC .................................. 607/116, 120–122, 149
See application file for complete search history.

(56) References Cited

U.S. PATENT DOCUMENTS

| | | | |
|---|---|---|---|
| 4,827,940 A * | 5/1989 | Mayer et al. .................. 600/375 |
| 5,383,924 A | 1/1995 | Brehier | |
| 6,330,481 B1 | 12/2001 | Van Wijk et al. | |
| 6,419,674 B1 | 7/2002 | Bowser et al. | |
| 2004/0215306 A1 | 10/2004 | Heil, Jr. et al. | |
| 2008/0103578 A1 | 5/2008 | Gerber | |
| 2008/0103579 A1 | 5/2008 | Gerber | |
| 2009/0192571 A1* | 7/2009 | Stett et al. ........................ 607/54 |
| 2009/0318849 A1 | 12/2009 | Hobbs et al. | |

OTHER PUBLICATIONS

Hauser, Robert G., Kallinen, Linda M., Katsiyiannis, William T., "Deaths and Serious Injuries Associated with ICD and Pacemaker Lead Extraction", Minneapolis Heart Institute Foundation (15 pages).

European Search Report and Notes to the European Search Report on European Patent Application No. EP 11 19 4027, dated May 15, 2012 (5 pages).

* cited by examiner

*Primary Examiner* — Michael Kahelin
*Assistant Examiner* — Mallika D Fairchild
(74) *Attorney, Agent, or Firm* — Buchanan Ingersoll & Rooney PC

(57) ABSTRACT

The present disclosure relates to permanently implantable electrode structures or probes of the type used, in particular, in cardiac pacemakers, ICDs, CRT-Ds and/or neurostimulators. Such electrode structures or probes include at least one control element, the physical-chemical state of which can be specifically manipulated using external excitation, such that local degradation or dissolution of a part of the implant or the entire implant takes place in this region. As a result of this partial dissolution, for example, the electrode structure or at least a portion thereof is modified such that the conditions for explantation are improved and/or parts of an implanted electrode structure that remain in the body are functionally deactivated.

18 Claims, 7 Drawing Sheets

- Prior Art -

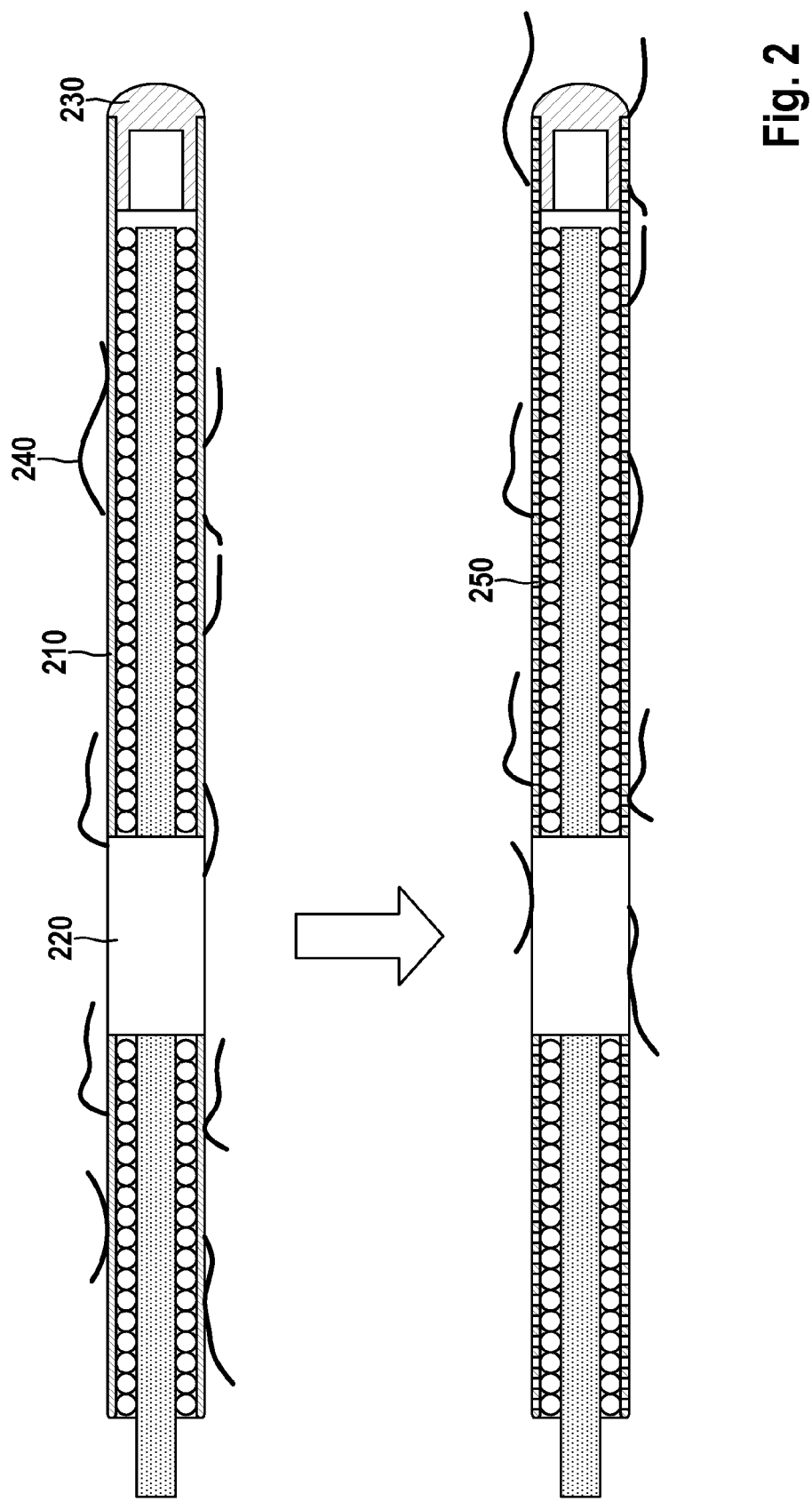

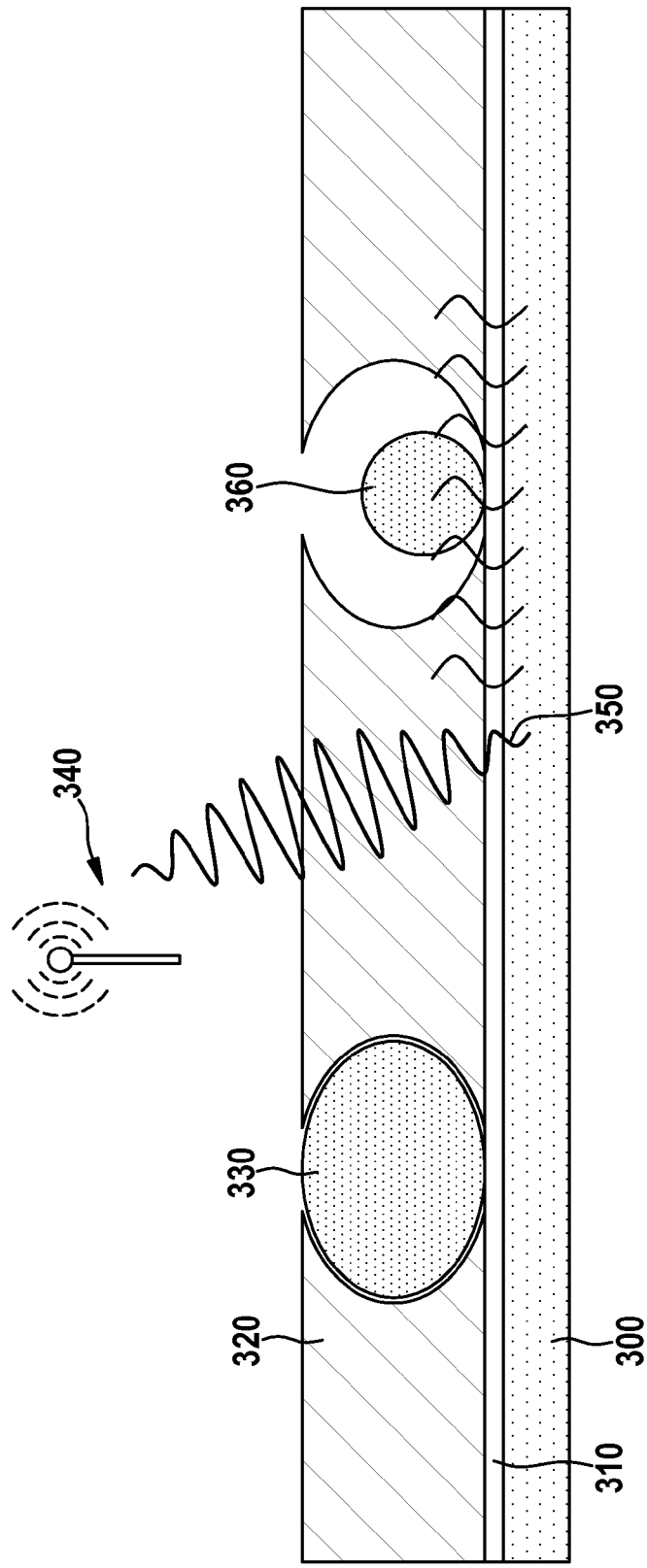

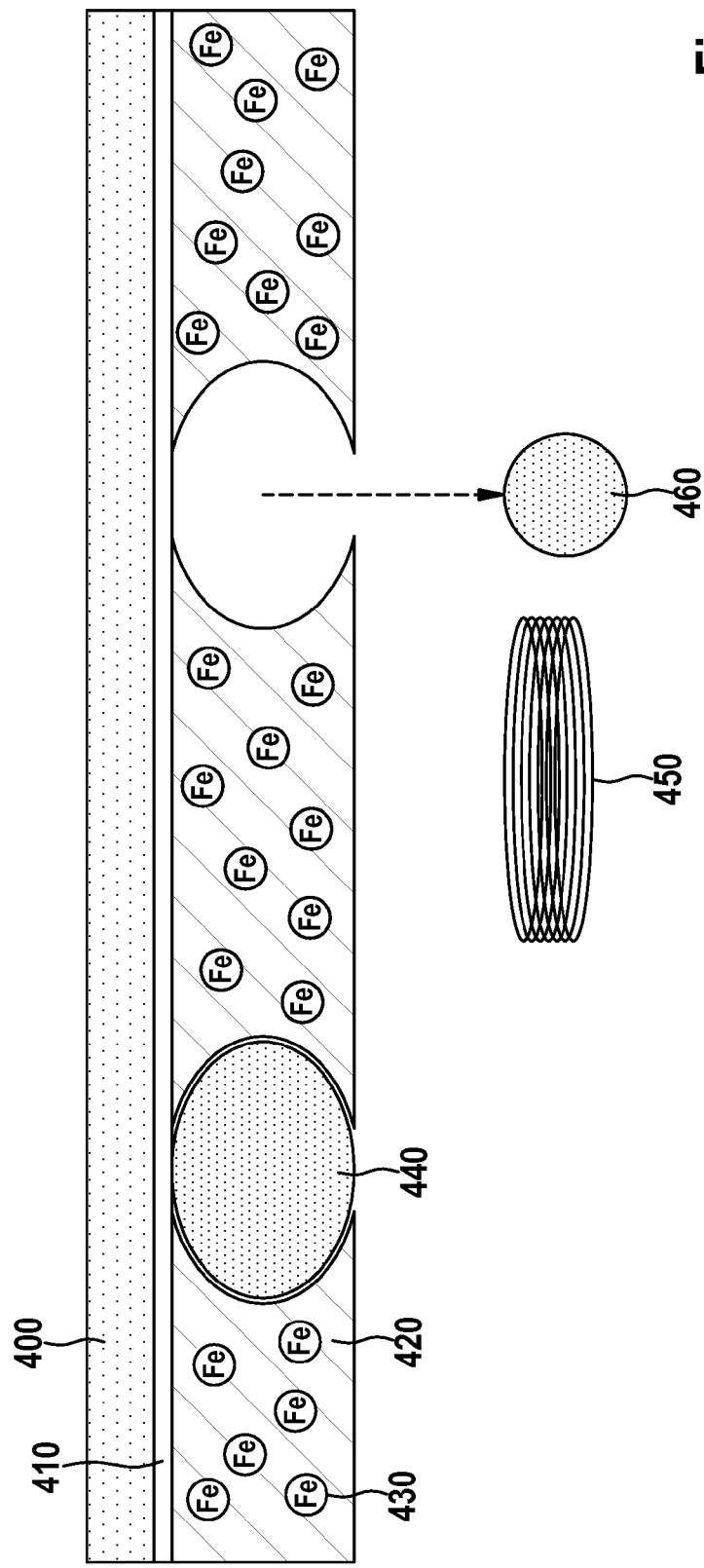

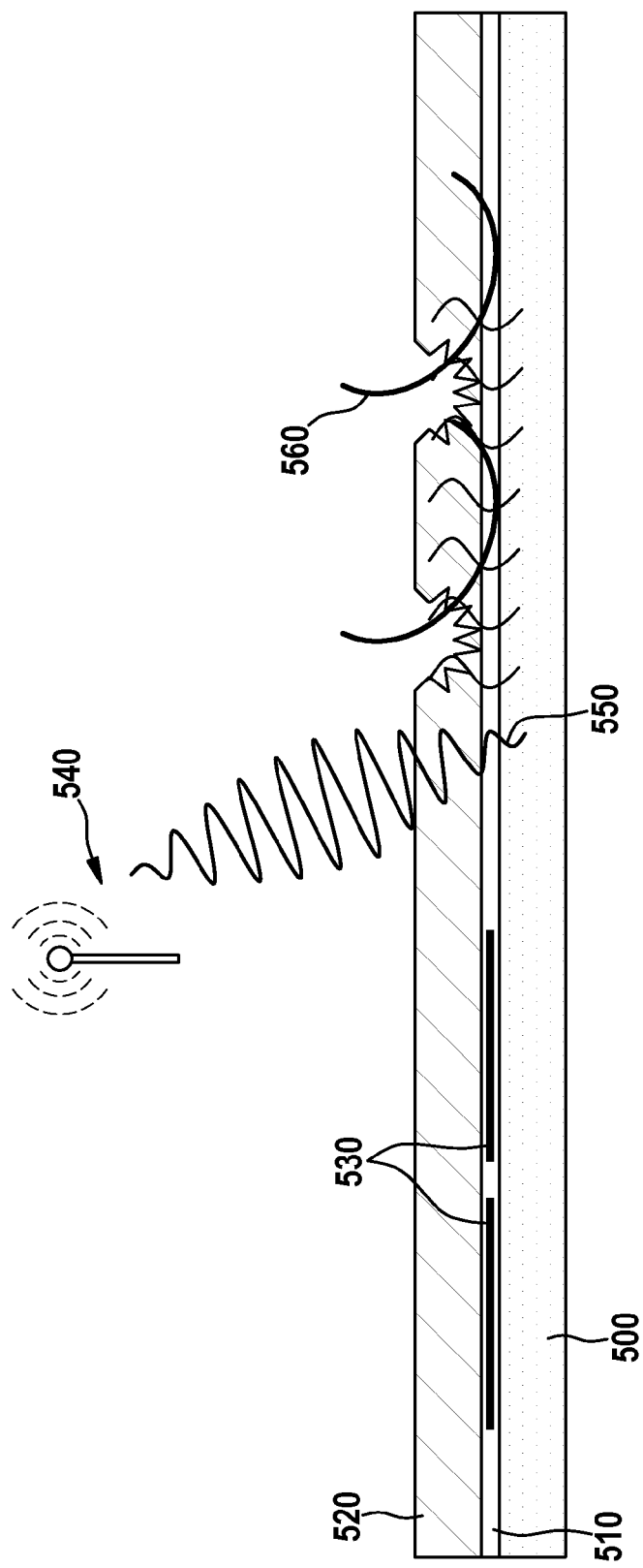

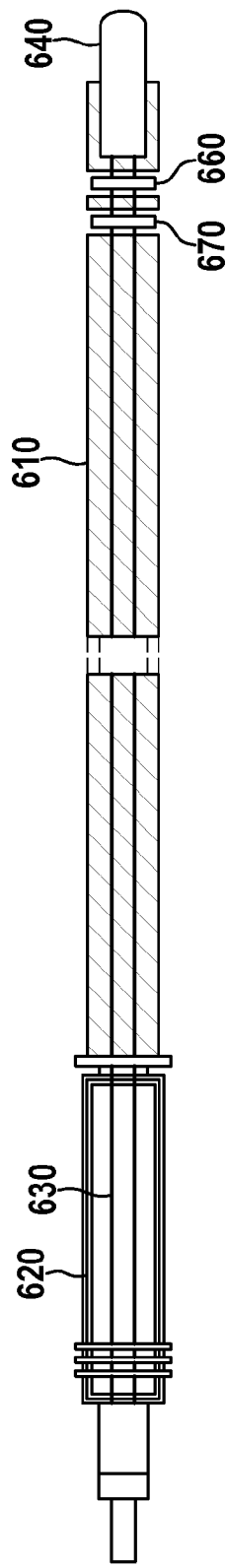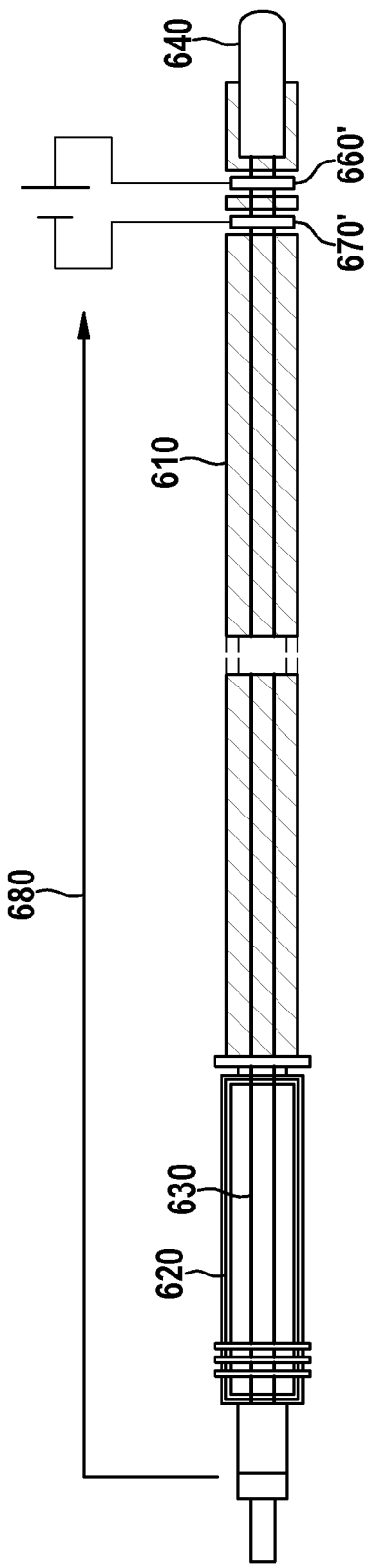

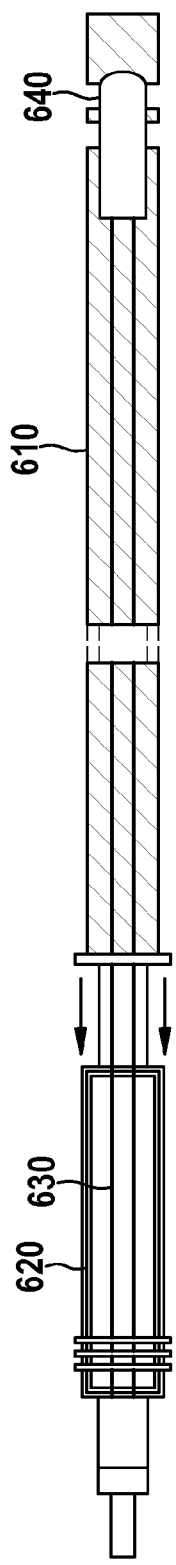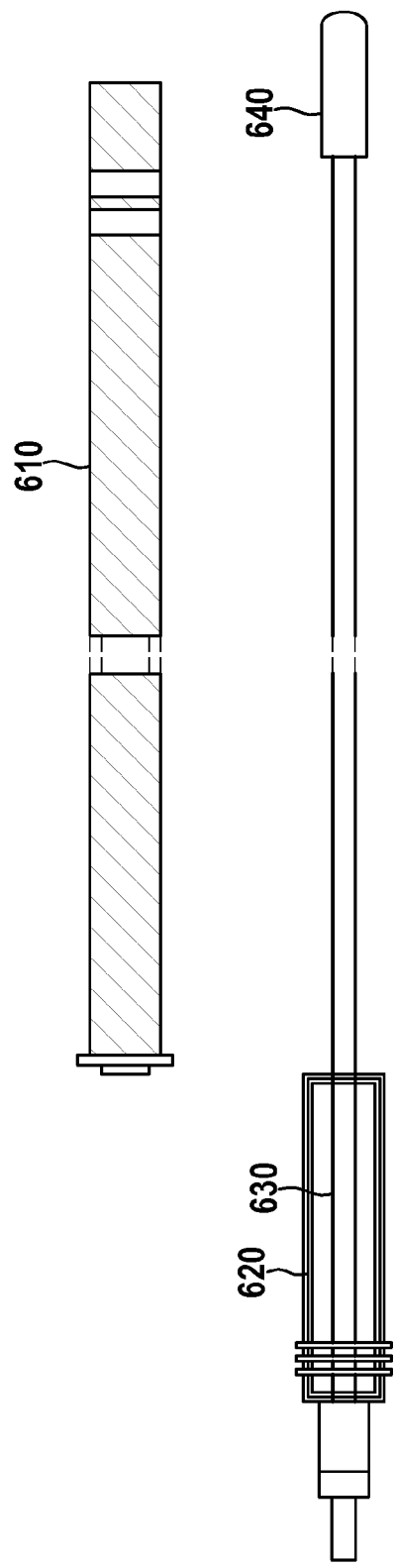

SELF-DISSOLVING ELECTRODE OR PROBE IMPLANT

RELATED APPLICATION

This patent application claims the benefit of U.S. Provisional Patent Application No. 61/432,213, filed on Jan. 13, 2011, which is hereby incorporated by reference in its entirety.

TECHNICAL FIELD

The present disclosure applies to the field of human medicine. It relates to electrode arrangements or probes that are used as an implant in the human body.

BACKGROUND

Such implants have been used in diverse embodiments in modern medical technology and are used, e.g., in cardiac pacemakers, ICDs, CRT-Ds and neurostimulators.

In regard to permanently implantable electrode leads or probes, it is known that parts of the implant can fuse at least partially with endogenous tissue due to the longer residence times in the human body. To reduce this unwanted effect, electrodes or probes are currently provided with surface coatings that are inhibitive in this regard. For example, it is known that a steroid elution counteracts adhesion of electrodes or probes to endogenous tissue. In addition, to improve explantation properties, an objective is to create a surface of the implant that is as entirely smooth as possible, e.g., by embedding the shock coil of an ICD electrode in the electrode body. As an additional measure, an implant design that is isodiametric or tapers in the distal direction is frequently selected.

Despite these measures, adhesion of electrode leads or probes in endogenous tissue cannot be fully prevented over the long term. This can lead to difficulties when performing explantations, since it cannot be ruled out that parts of the tissue will be destroyed in the process. Such tissue damage can lead to serious complications depending on the region of the body that is involved.

A particularly critical situation is depicted in FIG. 1. In this case, as an example, an endocardial ICD electrode 110 is implanted in human heart 100. It comprises a distal shock coil 120 situated in the right ventricle of the heart 100 and a proximal shock coil 130 disposed largely in the superior vena cava 140 at the outlet of the right atrium. Due to the helical design and despite shape and surface optimization, adhesion 150 of the shock coil with the vascular walls takes place with the majority of these electrodes. In the case of a probe extraction, such adhesions with the vascular wall of the vena cava pose the greatest risk since a vascular rupture of the vena cava can occur here very rapidly. See e.g., Hauser et al., "Deaths and Serious Injuries Associated with ICD and Pacemaker Lead Extraction", 30 (Abstract Supplement) 277, European Heart Journal (2009).

On the other hand, leaving deactivated electrodes or probes in the body is not unproblematic, as considered from other perspectives. If such implants are left in the body, complications such as vascular occlusions, interactions of a deactivated electrode with active electrodes, or a contraindication to MRT can result.

The problem addressed by the present inventive disclosure is therefore that of developing permanently implantable electrode leads or probes that are performed to ensure that the explantation thereof can be performed in a substantially easier manner, or that the occurrence of resultant complications is notably reduced if left in the body.

The present inventive disclosure is directed toward overcoming one or more of the above-identified problems.

SUMMARY

This problem is solved in the case of a permanently implantable electrode or probe having the features of the independent claim(s). Further features of advantageous embodiments of the present disclosure are the subject matter of the dependent claims.

According to the subject matter of the disclosure, an implantable electrode lead or probe comprises at least one control element, the physical-chemical state of which can be manipulated using external excitation such that local degradation or dissolution of a part of the implant or the entire implant—even as a result of the local degradation—takes place in this region. As a result of this process, for example, existing adhesions of an electrode implant with bodily tissue are separated by surface regions of the implanted electrode dissolving at least partially in the region of the adhesions. As an alternative, a stimulated local dissolution of a region of an implanted electrode or probe can be used to taper electrode structures at preferred points, thereby making explantation substantially easier. In the same manner, predetermined breaking points can be specifically created, thereby making it possible to remove substantial parts of an implant without causing significant damage to the tissue.

The placement and number of regions that can be stimulated to degrade or dissolve by way of the external excitation of control elements can be varied within wide limits depending on the type and application of the implant. For example, either only predefined points or parts of the existing electrode structure or probe can be excited to dissolve while other regions remain unchanged, or, for example, the dissolution process induced by stimulation can affect an entire implanted electrode or probe, thereby reducing the volume thereof overall or even completely dissolving the electrode or probe.

Various other objects, aspects and advantages of the present inventive disclosure can be obtained from a study of the specification, the drawings, and the appended claims.

DESCRIPTION OF THE DRAWINGS

The inventive subject matter will be described in greater detail in the following using preferred embodiments, with reference to the drawings and the reference characters noted therein. In the drawings:

FIG. 2 is a schematic depiction of an electrode implant with local tissue adhesion and explantation of the electrode after stimulated partial dissolution of an outer layer.

FIG. 3 is a first embodiment of an outer layer of an implantable electrode or probe, which can be degraded using external excitation.

FIG. 4 is a second embodiment of an outer layer of an implantable electrode or probe, which can be degraded using external excitation.

FIG. 5 is a third embodiment of an outer layer of an implantable electrode or probe, which can be degraded using external excitation.

FIG. 6 is an alternative embodiment of an electrode implant that can be partially dissolved using external stimulation.

FIG. 7 is a schematic depiction of the externally excited dissolution of a part of the electrode implant according to FIG. 6.

FIG. 8 is a schematic depiction of the extraction of the inner electrode structure after dissolution of a part of the electrode implant according to FIG. 6.

FIG. 9 is separated subcomponents of the electrode implant according to FIG. 6

DETAILED DESCRIPTION

Figure 1:
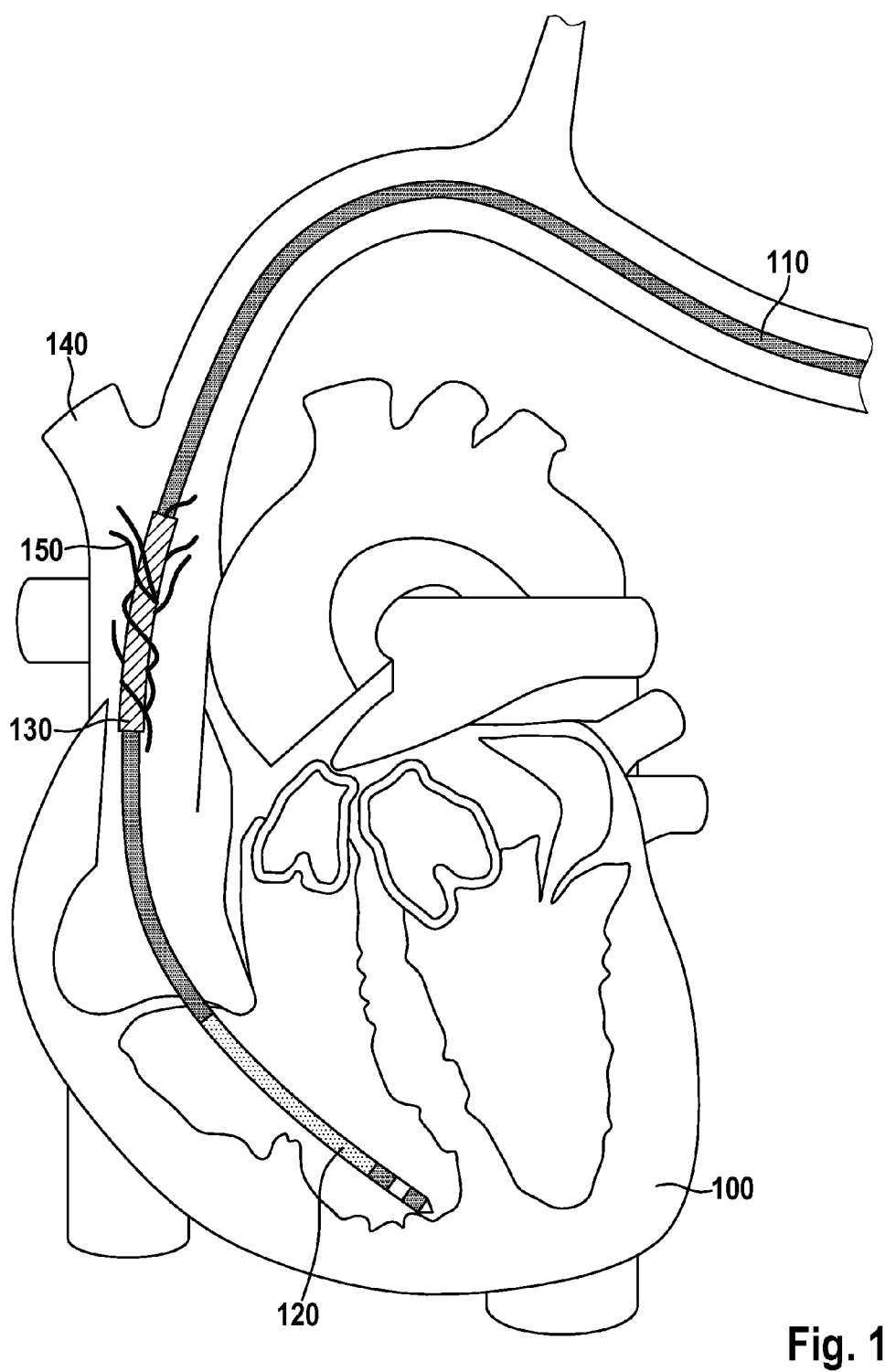
FIG. 1 is a schematic depiction of an endocardial ICD electrode implanted in the human heart, with local tissue adhesion.

FIG. 2 shows the distal part of an electrode arrangement comprising outer insulation 210. This outer region is typically comprised of a material having the greatest possible biocompatibility. "Biocompatibility" refers to the capability of a material to evoke an appropriate tissue response in a specific medical application. This includes an adaptation of the chemical, physical, biological, and morphological surface properties of an implant to the recipient tissue, with the objective of establishing a clinically desired interaction. The biocompatibility of the implant material is furthermore dependent on the timing of the response of the biosystem in which the implant is placed. For example, irritations and inflammations, which can cause tissue changes, occur over the relatively short term. Biological systems therefore respond differently depending on the properties of the implant material. Depending on the response of the biosystem, implant materials can be subdivided into bioactive, bioinert, and degradable/resorbable materials.

The electrode arrangement depicted in FIG. 2 comprises two stimulation poles (ring 220 and tip 230). Endogenous tissue 240 has grown around the electrode lead to a large extent, thereby preventing it from being explanted simply by pulling it out. According to the inventive disclosure, in this embodiment, outer insulation layer 210 comprises regions 250 in which a degradation process of the insulation layer can be triggered by external excitation of control elements. Due to the partial or complete dissolution of these regions 250 of the insulation layer 210, the adhesion between the surface of the insulation layer 210 of the implanted electrode and the surrounding endogenous tissue 240 is considerably reduced, and the risk of tissue being damaged upon explantation by the implant being pulled out is markedly reduced.

FIG. 3 shows a schematic depiction of a first embodiment of an implantable electrode or probe which, according to FIG. 2, comprises an outer coating which, according to the inventive disclosure comprises regions that can be degraded by external excitation. An insulation layer 320 is applied, at least in sections, on inner electrode structure 300 e.g. using a primer 310. Insulation layer 320 is generally not biocorrodible and can contain, e.g., poly-L-lactide or be composed thereof, or another representative of the polyesters, such as, but not limited to, PDLLA, PLGA, P3HB, P4HB or mixtures or copolymers thereof. As an alternative or in addition thereto, the protective layer can contain Parylene (Parylene C or other derivatives), preferably as Parylene with "pin holes". In addition thereto or instead thereof, the protective layer can comprise cellulose, preferably as a film, such as, e.g., nitrocellulose, methylcellulose and/or carboxymethyl cellulose. The protective layer can also comprise polyvinyl alcohols, wherein a film formation can be optimized by selecting the molar mass and the degree of deacetylation accordingly. Polyvinyl alcohol is a crystalline polymer that is lightly branched due to the manufacturing process thereof. Polyvinyl acetate is manufactured from vinyl acetate. Polyvinyl acetate is hydrolyzed to form polyvinyl alcohol by reaction with bases. The melting and glass transition temperature depends not only on the degree of hydrolysis and the molar mass, but also on the distribution of acetyl groups (statically or in blocks), the tacticity, and the water content of the polymer. Polyvinyl alcohols having high to moderate degrees of hydrolysis and degrees of polymerization up to 2000 are suitable. The films made from polyvinyl alcohol are tear-resistant and viscoplastic. They are resistant to oil and heat. Polyalcohols such as glycerol and ethylene glycol can be used as softening agents.

Insulation layer 320 comprises control elements in the form of perforation points 330 which are filled with a hydrogel. A hydrogel is a polymer that contains water but is insoluble in water, the molecules of which are coupled either chemically, e.g., by covalent or ionic bonds, or physically, e.g., by forming loops of the polymer chains to form a three-dimensional network. Hydrogels according to the inventive disclosure are capable of undergoing changes in volume in response to external excitation in that they have a variable swelling capacity and can therefore absorb quantities of water per mmol of hydrogel polymer that differ in a controllable manner.

These hydrogels can be made, e.g., by reacting ethylenically unsaturated monomers and polymers which carry ionizable groups with cross-linking agents and polymerization catalysts. As an alternative thereto, suitable hydrogels can be made using condensation reactions with difunctional and multifunctional monomers. Suitable monomers and polymers and methods for their manufacture are known to a person skilled in the art and need not be described in detail herein. Likewise, methods for the manufacture of suitable hydrogels using such monomers or polymers or combinations thereof are also known to a person skilled in the art and will not be described in detail herein. Preferable hydrogels contain, for example, a polymer based on acrylamide, methacrylamide, dimethylaminoethyl methacrylate, or a derivative of acrylamide, methacrylamide, or dimethylaminoethyl methacrylate. Other preferred hydrogels contain, for example, a polymer based on poly(N-isopropylacrylamide) or poly-N-isopropylacrylamide-co-allylamine or poly(N-isopropylamide) (PNIPAM) or mixtures thereof with poly(p-dioxanon) as the hard segment.

The expression "swelling capacity" according to the inventive disclosure refers to the property of the hydrogel to absorb a certain quantity of water per mmol of hydrogel polymer. Reduced swelling capacity results in a reduction of the volume of the hydrogel and, therefore, to a change in shape of the hydrogel. Suitable methods and measurement procedures for determining the swelling capacity are known to a person skilled in the art; measurement procedures that have already been proven repeatedly in the field of galenics are particularly suitable.

Preferably, hydrogels are used that have a temperature-depending swelling capacity. Particularly preferred hydrogels have a swelling capacity that diminishes as the temperature rises. Such hydrogels can be, for example, those wherein their swelling capacity diminishes by at least 30%, preferably by up to 50%, and particularly preferably by 30% to 50%, given a temperature increase of approximately 10K.

The temperature dependence of the hydrogel is preferably selected such that it has a pronounced hysteresis effect in regard to the swelling properties and, therefore, the swelling capacity remains reduced even after return to a starting temperature of approximately 37° C.

As depicted schematically in FIG. 3, in this embodiment, a temporary heating of insulation layer 320 and, therefore, the hydrogel, can be initiated in perforation points 330 via external impression of high-frequency energy using, for example, a high-frequency transmitter 340. Preferably, the wavelength of high-frequency transmitter 340 is matched to the antenna geometry 350 of the electrode structure, thereby ensuring that heating is effective. The induced heating of the electrode structure also warms the hydrogel and reduces the swelling properties thereof to the extent that the hydrogel undergoes a deformation resulting in a reduced hydrogel volume 360, thereby largely exposing perforation point 330 in insulation layer 320. Given an appropriate number of such perforation points 330, the reduction of the hydrogel volume results in a considerable overall reduction in the adhesion between the surface of insulation layer 320 and the surrounding endogenous tissue.

FIG. 4 shows an alternative embodiment of an outer layer of an implantable electrode or probe, which can be degraded using external excitation. In this case as well, an insulation layer 420 having perforation points 440 is applied to electrode structure 400 of an implant using primer 410. Insulation layer 420 contains magnetic nanoparticles 430. Perforation regions 440 are also closed in this embodiment using a hydrogel. In this embodiment, a hydrogel having a discontinuous swelling capacity is used, which abruptly collapses to a reduced hydrogel 460 above a certain temperature (e.g., above 45°-50° C.), and thereby "drops out" of the perforation point 440 of the protective layer. Insulation layer 420 and, therefore, the hydrogel, are heated in this case using, for example, an alternating magnetic field which is impressed by an external magnetic alternating field generator 450. Magnetic nanoparticles 430 are induced to oscillate by the alternating magnetic field, thereby heating insulation layer 420 and the hydrogel in perforation points 440.

In the embodiments depicted in FIGS. 3 and 4, once external excitation has taken place and perforation points 330, 440 have therefore been opened, bodily medium can also reach inner electrode structure 300, 400 provided adhesion bridge 310, 410 has been performed to be permeable thereto. If a biocorrodible metallic material is selected in addition for inner electrode structure 300, 400, then, due to contact with bodily medium, the degradation process triggered by external excitation also affects inner electrode structure 300, 400 in the regions in which insulation layer 320, 420 has perforation sites 330, 440. A "bodily medium" according to the inventive disclosure is understood to be all media that are naturally present in the human body or that are additionally incorporated via absorption into the body. This includes, but is not limited to, fluids that contain water, such as blood, lymph, saliva and other substances, in particular ions, and also includes gasses, such as, for example, carbon dioxide, hydrogen, oxygen, and nitrogen.

In the field of biocorrodible metallic materials, magnesium or pure iron are typically used, as are biocorrodible base alloys of the elements magnesium, iron, zinc, molybdenum, tungsten, or aluminum. In addition, alloys of the aforementioned base elements additionally comprising one element from the group of alkaline metals or alkaline-earth metals are known. Alloys based on magnesium, iron and zinc are described as being particularly suitable. Minor constituents of the alloys can be, for example, manganese, cobalt, nickel, chromium, copper, cadmium, lead, tin, thorium, zirconium, silver, gold, palladium, platinum, silicon, calcium, lithium, aluminium, zinc and iron. Particularly suitable is the use of a biocorrodible magnesium alloy having a portion of magnesium >90%, yttrium in the range 3.7-5.5%, rare earth metals in the range 1.5-4.4%, and the rest <1% of other materials.

By combining a coating which is locally degradable by external excitation of control elements and an electrode structure comprised of biocorrodible material, predefined parts of an implanted electrode structure—or the entire electrode structure—can be specifically incorporated in a corrosion process by arranging the degradation points accordingly.

FIG. 5 shows a schematic depiction of another embodiment of the inventive disclosure, in the case of which, after external excitation of control elements, degradation of local regions of an insulation layer begins and, due to the formation of pores, contact of bodily fluid with inner electrode structures of the implant is induced. In this embodiment as well, an insulation layer 520 is applied to inner electrode structure 500 of the implant using primer 510. In this embodiment, primer 510 also contains molded bodies 530 as control elements which are comprised of a biocompatible, and preferably biodegradable, memory-effect polymer. Memory-effect polymers are plastics that have a so-called "shape memory" effect. A "shape memory" effect is understood to mean that a memory-effect polymer can be stably transferred from an original shape into another shape in which it remains until the memory-effect polymer returns to a previous shape or the original shape, e.g., in response to external excitation.

In the embodiment shown, the original shape of the memory-effect polymer is curved, and the planar shape of molded body 530 is the "deformed state" (set at approximately 125° C.) of the memory-effect polymer. Electrode structure 500 and, therefore, adjacent molded bodies 530 are heated to approximately 45° C. for at least 10 seconds using, for example, a high-frequency energy impressed using an external high-frequency transmitter 540. Preferably, the wavelength of the high-frequency transmitter 540 is matched to the antenna geometry 550 of the electrode structure, thereby ensuring that heating is effective. The memory-effect polymer of molded body 530 thereby assumes its original, curved shape, as shown at 560. Insulation layer 520 is partially perforated by molded bodies 560, the shape of which has now been changed, and bodily fluid reaches inner electrode structure 500 in this region.

As an alternative, the deformation of the memory-effect polymer can also be triggered by light in this case. According to one conceivable application, the deformation is triggered by irradiation of UV light having a wavelength of less than 260 nanometers, e.g., using fiber optic catheters.

FIGS. 6-9 show an alternative embodiment of an electrode structure that can be partially dissolved using external stimulation. The implant is comprised of an outer insulation tube 610, a bipolar electrode connector 620, metallic electrode leads 630, and at least one electrode pole 640. In the configuration shown, the leads and the electrode head having metallic fixators 660, 670 are securely connected in the distal region to the external insulator, and therefore the electrode structure forms a stable unit.

In the case of this embodiment, as shown in FIGS. 6-9 and according to the inventive disclosure, before explantation of this electrode structure, the region of fixators 660, 670, as control element, can be specifically excited externally. This is depicted in FIG. 8. By application of an appropriate voltage 680, via electrode connector 620, the potential difference initiates corrosion of the fixators (660', 670'). Depending on the duration of exposure to external excitation, fixators 660, 670 are thereby weakened or, as shown in FIG. 8, are even fully dissolved and the inner electrode structure can be pulled out relative to outer insulation 610.

As shown in FIG. 9, the initially one-piece electrode implant breaks down into two separable components due to the degradation of the local region 660, 670 induced by external excitation. All conductive components, i.e., electrode connector 620, metallic electrode leads 630, and electrode pole 640, can therefore be extracted. Outer insulation layer 610 can then also remain in the body and be used as an introduction channel, e.g., for a new electrode.

A region which can be introduced to local corrosion according to the inventive disclosure using external excitation of control elements, as illustrated in FIGS. 7 to 9, can be provided at various predefined points of an implantable electrode structure or probe. It is therefore possible to specifically electrolytically dissolve various regions of the electrode structure by applying appropriate external voltage using different potential differences. The rate of the individual dissolution process can be controlled by the selection of the metallic material and the potential difference. The procedure can therefore be adjusted such that compatibility for the human organism is ensured during the dissolution procedure.

The external excitation of control elements as the trigger for degradation processes at specified regions of implantable electrode structures or probes can also take place, in an alternative manner, by the administration of drugs or the application of special chemical substances that induce dissolution of local regions of the electrode structure, e.g., by catalytic action. For this purpose, an implanted electrode structure comprises appropriate regions of selected materials at the desired points, which enter into physical/chemical interaction with the added substances in the sense of degradation.

All of the embodiments of the inventive disclosure shown can also be combined, and therefore, e.g., regions can be provided on an electrode structure that degrade by external HF excitation, but regions can also be present that corrode electrolytically using an externally applied potential difference.

Although certain embodiments have been illustrated and described herein, it will be appreciated by those of ordinary skill in the art that a wide variety of alternative or equivalent embodiments or implementations, calculated to achieve the same or similar purposes, may be substituted for the embodiments illustrated and described herein without departing from the scope of the present invention. Those of skill in the art will readily appreciate that embodiments in accordance with the present invention may be implemented in a very wide variety of ways. This application is intended to cover any and all adaptations and/or variations of the embodiments discussed herein.

The terms and expressions which have been employed in the foregoing specification are used therein as terms of description and not of limitation, and there is no intention, in the use of such terms and expressions, to exclude equivalents of the features shown and/or described or portions thereof, it being recognized that the scope of the invention is defined and limited only by the claims that follow.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. A system comprising:
    an implantable electrode or probe adapted to be implanted in a body of a person, the implantable electrode or probe comprising:
        a metallic electrode structure;
        an external protective layer at least partially enclosing the metallic electrode structure, the external protective layer comprised of a biocompatible material, has insulating electrical properties, and is impermeable to bodily medium; and
        at least one control element, at least one of the physical and chemical state of which can be modified using external excitation such that local degradation at least of a part of the external protective layer takes place in the region of the at least one control element; and
    a source of excitation adapted to be located external to the body of the person in whom the electrode or probe is adapted to be implanted, the external source supplying the external excitation,
    wherein the at least one control element is integrated in the protective layer such that the degradation triggered locally by the external excitation affects a region of the protective layer, and
    wherein the degradation comprises forming a local perforation in the protective layer.

2. The system according to claim 1, wherein the at least one control element is performed, via the shape and placement thereof, as a mechanical attachment of the electrode structure relative to the surrounding protective layer, and wherein the dissolution triggered by external excitation undoes the attachment of the electrode structure relative to the surrounding protective layer in the region of the at least one control element.

3. The system according to claim 1, wherein the at least one control element is designed as a defined part of the electrode structure, and wherein the external excitation in the region of the at least one control element triggers local degradation of the protective layer by electrolytic corrosion.

4. The system according to claim 3, wherein the external excitation comprises an electric voltage supplied to the control element using the electrode structure.

5. The system according to claim 1, wherein the modification of at least one of the physical and chemical state of the at least one control element induced by external excitation comprises a deformation.

6. The system according to claim 1, wherein the at least one control element comprises a hydrogel or is composed thereof.

7. The system according to claim 6, wherein the swelling capacity of the hydrogel is temperature-dependent, wherein the swelling capacity diminishes as temperatures increase.

8. The system according to claim 7, wherein the swelling capacity of the hydrogel diminishes by at least 30% given a temperature increase of 10K.

9. The system according to claim 7, wherein the swelling capacity of the hydrogel has a hysteresis.

10. The system according to claim 1, wherein the at least one control element comprises a memory-effect polymer or is composed thereof.

11. The system according to claim 1, wherein the external excitation comprises electromagnetic radiation.

12. The system according to claim 11, wherein the electromagnetic radiation comprises high-frequency radiation or light, ultrasound, ionizing radiation, or a magnetic field.

13. The system according to claim 1, wherein the protective layer is comprised at least partially of a biocorrodible material, which is at least partially dissolved upon contact with bodily medium as a consequence of the degradation of the protective layer.

14. The system according to claim 13, wherein the biocorrodible material comprises a magnesium alloy.

15. The system according to claim 1, wherein the external excitation comprises the administration of drugs or chemical substances which enter into interaction with the at least one control element, thereby modifying at least one of the physical and chemical state thereof.

16. The system according to claim 1, wherein the electrode or probe implant is permanently implantable.

17. The system according to claim 1, wherein the at least one control element comprises a biodegradable preformed body in a first shape provided as a mechanical attachment of the electrode structure relative to the surrounding protective layer, and wherein the dissolution triggered by external excitation causes the at least one control element to assume a second shape forming the local perforation in the protective layer.

18. The system according to claim 17, wherein the biodegradable preformed body is made of memory-effect polymer.

\* \* \* \* \*